(12) United States Patent
Anschel

(10) Patent No.: US 8,777,405 B2
(45) Date of Patent: *Jul. 15, 2014

(54) SELF-ADHERING VISUAL STIMULATOR

(76) Inventor: David Joseph Anschel, Rocky Point, NY (US)

( * ) Notice: Subject to any disclaimer, the term of this patent is extended or adjusted under 35 U.S.C. 154(b) by 230 days.

This patent is subject to a terminal disclaimer.

(21) Appl. No.: 13/169,694

(22) Filed: Jun. 27, 2011

(65) Prior Publication Data

US 2012/0327367 A1   Dec. 27, 2012

(51) Int. Cl.
*G02C 1/00* (2006.01)
*A61B 13/00* (2006.01)

(52) U.S. Cl.
USPC ........................................... 351/158; 600/558

(58) Field of Classification Search
CPC ...... G02B 27/017; G02C 11/00; G02C 11/06; G02C 3/003
USPC ............... 351/158, 41; 600/558, 26, 27, 544; 607/1, 88, 91; 362/103, 800, 105
See application file for complete search history.

(56) References Cited

U.S. PATENT DOCUMENTS

| | | | |
|---|---|---|---|
| 4,618,230 A | 10/1986 | Ens et al. | |
| 4,676,611 A | 6/1987 | Nelson et al. | |
| 4,822,161 A * | 4/1989 | Jimmy | 351/158 |
| 4,858,609 A | 8/1989 | Cole | |
| 5,805,270 A | 9/1998 | Marshall | |
| 6,743,249 B1 | 6/2004 | Alden | |
| 7,862,516 B1 * | 1/2011 | Anschel | 600/558 |
| 2006/0136018 A1 | 6/2006 | Lack | |
| 2007/0200998 A1 * | 8/2007 | Schrimmer et al. | 351/158 |

OTHER PUBLICATIONS

Wiedemayer et al., "Visual Evoked Potentials for Intraoperative Neurophysiologic Monitoring Using Total Intravenous Anesthesia," Journal of Neurosurgical Anesthesiology vol. 15, No. 1, pp. 19-24 (2003).
Tobimatsu et al., "Studies of human visual pathophysiology with visual evoked potentials," Clinical Neurophysiology 117 (2006) pp. 1414-1433.

* cited by examiner

*Primary Examiner* — Hung Dang
(74) *Attorney, Agent, or Firm* — Hoffmann & Baron, LLP

(57) ABSTRACT

A device for the stimulation of the visual system includes a body having a pair of spaced lobes configured to conform to the periocular region. The body has a first side and an opposed second side. The body second side has an adhesive layer for securing the body to the periocular region. A light emitting source disposed within each of the pair of lobes to selectively illuminate the periocular region.

21 Claims, 6 Drawing Sheets

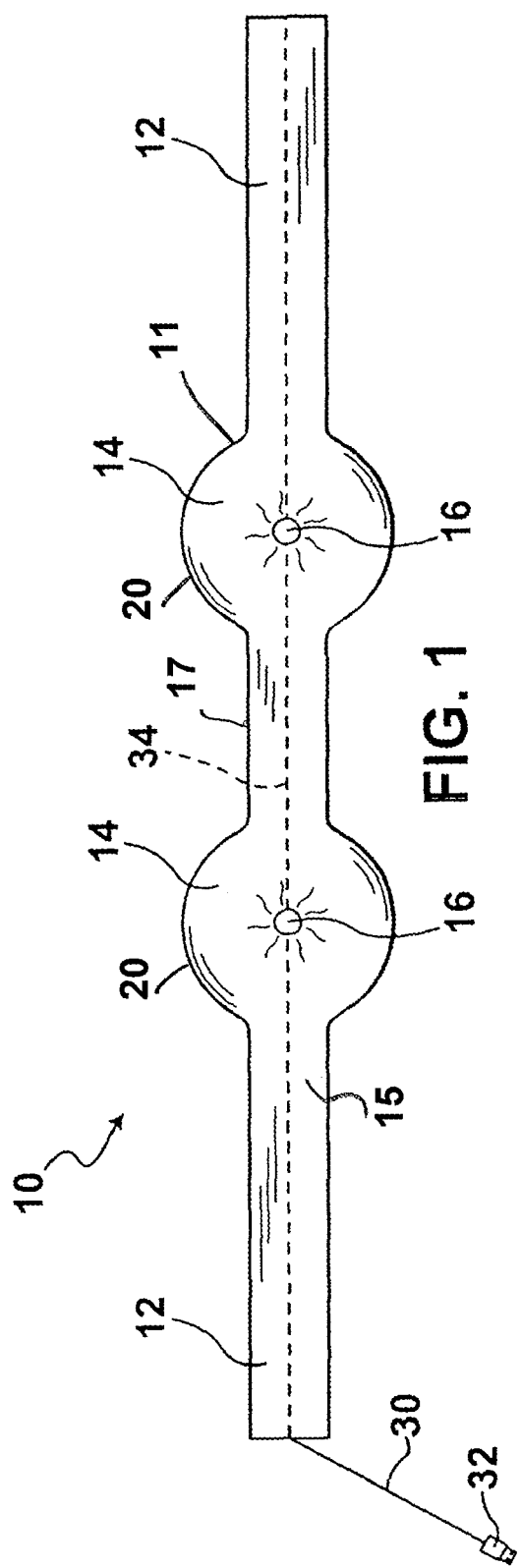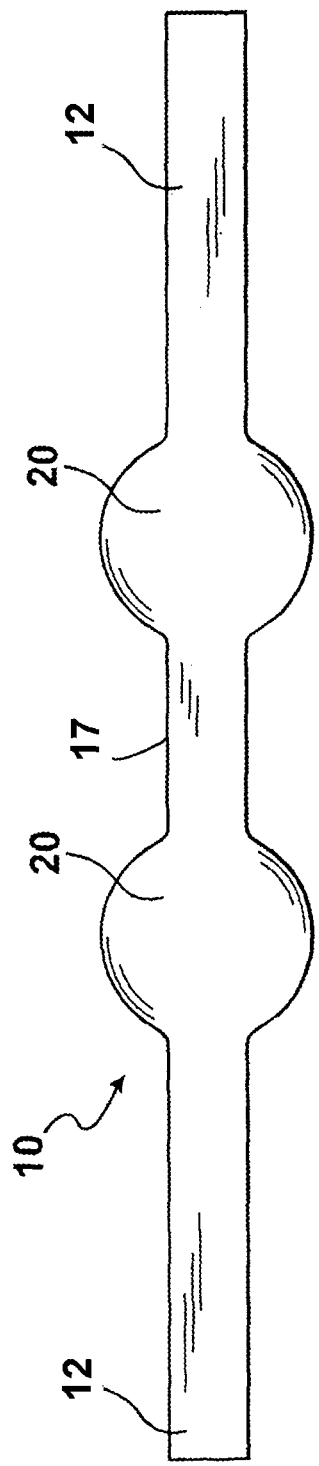

SELF-ADHERING VISUAL STIMULATOR

TECHNICAL FIELD

The present invention relates to the field of clinical neurophysiology. More specifically, the present invention relates to a device for the assessment of the visual system through the presentation of stimuli to the eyes. The purpose of such stimulating devices is the generation of the electroretinogram, nerve action potentials, visual evoked potentials/responses and similar neurophysiological parameters.

BACKGROUND

After entering the eyes, light passes through the lens and reaches the retina. Light will cause photoreceptor cells known as rods and cones to hyperpolarize. The photoreceptors synapse with other cells and eventually output is transmitted to the optic nerve.

The signal generated by the retina in response to a flash of light is known as the electroretinogram. This response may be recorded using conventional neurophysiological equipment and reflects overall retinal function.

The optic nerves from each eye progress medially as they pass into the vault of the skull and shortly reach the optic chiasm. It is along the course of the optic nerves that nerve action potentials may be measured intraoperatively. At the optic chiasm fibers from the temporal portion (nasal visual field) of the retina continue on ipsilaterally into the optic tract, while the nasal portion (temporal visual field) crosses the midline and enters the contralateral optic tract. The optic tract fibers then enter alternating layers of the lateral geniculate nucleus. Axons then project toward the cortex, thus forming the optic radiations, and eventually reaching the occipital cortex. It is this visual cortex which is responsible for generating the major components of what is commonly referred to as a visual evoked potential (visual evoked response).

The majority of routine clinical evoked potential testing is performed upon awake, cooperative subjects using an alternating checkerboard pattern as the stimulus. In order to be an effective stimulus, the subject must keep his eyes open and focus on the changing pattern. In those subjects who cannot cooperate, the alternating checkerboard pattern is not useful. Common examples of such subjects include the mentally impaired, young children, and those under the influence of anesthesia. Frequently a flashing light is used in order to obtain a response in such individuals. Additionally a flash is the typical way of eliciting an electroretinogram in order to assess retinal function. Electrodes are adhered to the scalp and the brain response is measured to determine if the brain is responding to the light. Such information can be used to determine the health of the eyes and optic nerves.

Monitoring the visual evoked potential is important during surgical operations, especially when the patient will be subject to anesthesia for a prolonged period. During such operations, damage to the optic nerve can take place, leading to postoperative blindness. By monitoring the evoked potential, the operating room staff can be alerted to any degradation to the optic nerve that might be occurring and take the necessary steps to correct the matter.

However, it has proven to be an exceptionally difficult task to employ such flash visual evoked responses in the operating room. A traditional strobe light is not feasible as it would be too distracting to the operating room staff and difficult to aim at the subject's eyes. Therefore, known methods of visual stimulation for the purpose of recording evoked responses (potentials) in uncooperative or anesthetized patients primarily rely upon the use of goggles with embedded light emitting diodes. These devices have shortcomings in that they are relatively unhygienic, fail to produce consistent responses in anesthetized patients, and pose a potential risk of damaging the eyes. Unfortunately, the results obtained with such equipment have been sub-optimal. Problems include: 1.) A reusable device must be cleaned in between patients, 2.) Tightly fitting goggles pose a risk of damaging the eyes, 3.) Goggles may fall off the eyes or move intraoperatively and be difficult to reposition once the procedure is underway, and 4.) The light emitting diodes utilized tend to be too weak to produce an adequate stimulus.

Accordingly, it would be desirable to provide a device securable to a subject which reliably provides a light stimulus and protects the eyes during the visual evoked potential testing.

SUMMARY

The present disclosure provides a device for the stimulation of the visual system including a body having a pair of spaced lobes configured to conform to the periocular region. The body has a first side and an opposed second side. The body second side has an adhesive layer for securing the body to the periocular region. A light emitting source disposed within each of the pair of lobes to selectively illuminate the periocular region.

The present disclosure further provides a visual stimulator including a frame configured to accommodate a wearer's periocular region. The frame has a first eye covering portion and a second eye covering portion. A light emitting source is disposed in the first and second eye covering portions. The light emitting source is operably connectable to a triggering device for operating the light emitting source in a predetermined sequence. The frame has a first side and an opposed second side. The frame first side includes a resilient portion engagable with and conformable to a wearer's periocular region. The resilient portion spaces the light emitting source from the frame first side, wherein the light emitting source is spaced from the wearer's periocular region.

The present disclosure still further provides a method for assessing visual pathways including:
providing a visual stimulator, wherein the visual stimulator comprises a body having resilient padding shaped to conform to a periocular region and an adhesive portion, at least one light emitting source disposed on the body, and a mechanism for interfacing with a triggering device;
adhering the visual stimulator to a periocular region;
stimulating the visual system by triggering the at least one light emitting source with the triggering device; and
detecting and recording neurophysiolocigal signals in response to the stimulating of the visual system.

BRIEF DESCRIPTION OF THE DRAWINGS

FIG. 1 is top elevational view of a first side of a visual stimulator with a single light emitting diode directed toward each eye.

FIG. 2 is top elevational view of a second side of a visual stimulator of FIG. 1.

DETAILED DESCRIPTION OF THE PREFERRED EMBODIMENTS

Figure 3:
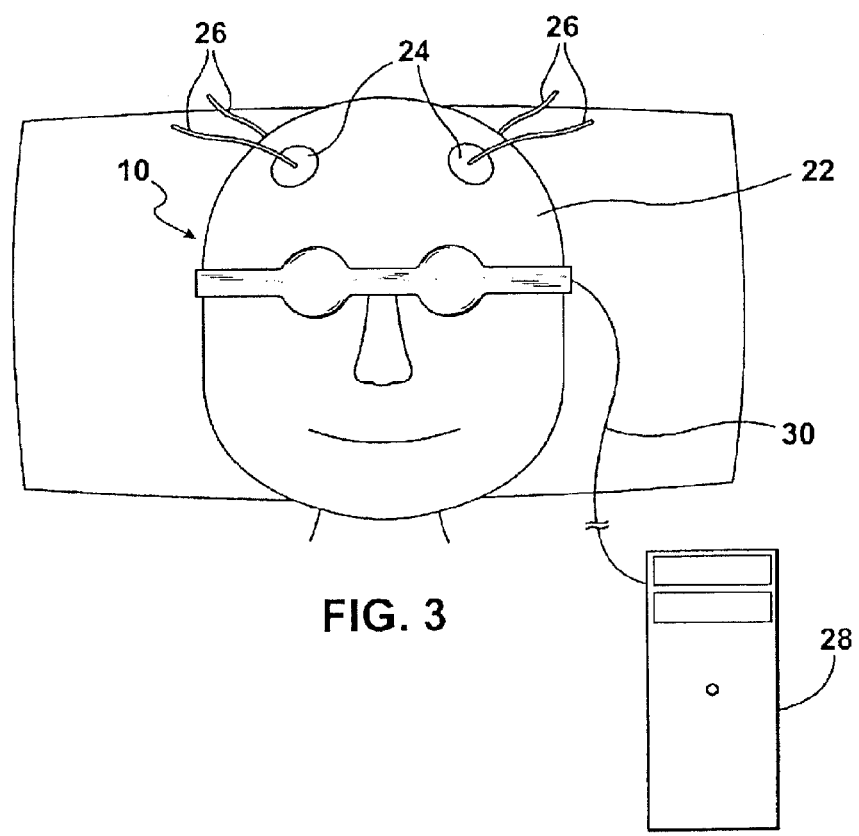
FIG. 3 is a top elevational view of the visual stimulator of FIG. 1 in place on a subject.

A device for stimulating the visual system is shown in FIGS. 1-3. The device may be a visual stimulator 10 having a frame body 11 including a soft resilient material 14. The visual stimulator 10 further includes a light source 16, such as light emitting diodes ("LEDs") at least partially surrounded by the soft resilient material 14. The frame 11 and resilient material 14 thereof may be specifically shaped to conform to the periocular region of the human face. The frame 11 may include a pair of eye covering portions 20 connected by a relatively narrow bridge portion 17. At least one light source 16 may be disposed on each of the eye covering portions 20. A surface of the frame body facing the periocular region may include an adhesive layer 15 for securing the visual stimulator 10 to the periocular region of a subject.

The light source 16 may be attached to a printed circuit board (not shown) or other interface to which the soft resilient material is secured. The visual stimulator 10 emits lights that stimulate the visual system for the recording of neurophysiological signals including the electroretinogram, optic nerve action potentials, and visual evoked potentials (visual evoked responses). This visual stimulator 10 provides several advantages over prior art, especially when employed in the operating room. These advantages include superior visual stimulation for the production of more reliable data, as well as improved safety and comfort for the subject.

FIG. 1 illustrates a first side of the visual stimulator 10 which will be placed toward the subject's eyes. The LEDs 16 are surrounded by specially shaped adhesive foam padding 14 which covers the eyes. Adhesive foam padding or other type of soft compliant material shaped to the contours of the periocular region. The specific thickness and composition of the padding may be customized, but for most applications will be between 5-20 mm in thickness and composed of polyurethane or similar material. Additionally other methods of attachment may be employed such as Velcro, clasps, snaps etc. For example, the visual stimulator may also include strap-like portions 12 that extend around the sides of the head. These straps 12 may include an adhesive layer such that they adhere to the sides of the head.

With reference to FIG. 2, the side of the visual stimulator 10 facing away from the subject has a similar appearance to the side facing the wearer, but the surface is non-adhesive and the light emitting diodes are covered by the rear components of the device 20. The portion of the device facing away from the patient may be opaque or semi-opaque so as to not transmit light away from the patient and towards others in the vicinity.

The light source 16 may consists of high intensity light emitting diodes or similar. It is within the contemplation of the present invention that the light emitting diodes may have varying configurations. For example, white or red LEDs may be directed at each eye or different color/wavelength light sources may be interspersed.

With reference to FIGS. 1 and 3, the visual stimulator is operably connected to a triggering device 28 via an interface mechanism 30. The interface mechanism may be wiring 30, 34 which would carry a signal from the triggering device 28 to the light emitting diodes 16. Wiring 34 may extend along a length of the visual stimulator 10 and be operably connected to the light emitting diodes 16. This wiring 34 may connect to wiring 30 which may terminate in a connector 32 that connects the visual stimulator to the triggering device 28. It is within the contemplation of the present invention that the connection between the visual stimulator and the triggering device may include wireless technology.

A shown in FIG. 3, the visual stimulator 10 may be placed over the eyes of the subject 22 on the periocular region of the face. The stimulator is attached to the subject's head 22 and is connected via wire 30 to the triggering device 28. The triggering device would energize the light source 16 in a predetermined sequence. Recording electrodes 24 are shown with wires 26 which would be attached to a data acquisition unit (not shown) of a type known in the art which would record the signals received from the subject in response to the emitted light. The recorded data may then be reviewed to monitor the subject's visual system.

Figure 4:
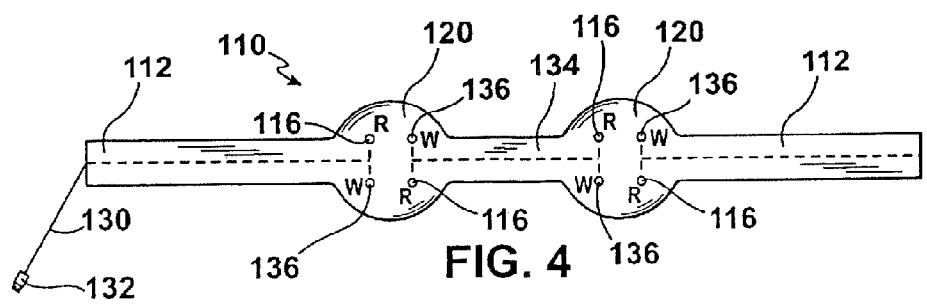
FIG. 4 is a top elevational a view of an alternative embodiment of the visual stimulator embodiment of the invention.

An alternative embodiment of the visual stimulator is shown in FIG. 4. In this embodiment, each eye covering portion includes a four light emitting diode array containing interspersed red 116 and white 136 light emitting diodes. The other features are identical to the embodiment described in FIGS. 1 and 2. The visual stimulator may include a pair of spaced generally round padded portions 120 with straps 112 extending therefrom. The light emitting diodes may be connected by wiring 132 which is connected to wiring 130. Wiring 130 may terminate in a connector 132 which would connect to the triggering device 28.

A further embodiment of the visual stimulator is shown in FIGS. 5-8. Visual stimulator 200 may be in the form of a visor-like member including a frame body 202. The frame 202 has a first side 204 and an opposed second side 206. The first side 204 faces and engages a subject's periocular region when the stimulator is worn.

The first side 204 may include a resilient material 208 which acts as padding that can conform to the wearer's features. The resilient material 208 permits the visual stimulator to firmly and comfortably engage the wearer. In one embodiment the frame 202 itself may be formed of a resilient material, such as foam. However, it is within the contemplation of the present invention that the resilient material may be formed separately from the frame and secured thereto. The resilient material 208 allows the frame to closely conform to the subject's periocular region and provide a comfortable soft interface with the subject.

The resilient material 208 may include an adhesive portion 210 which is used to secure the visual stimulator 200 to the user. Therefore, the need for straps or other securing devices is not required. The adhesive portion 210 may be in the form of a layer of adhesive applied to the resilient material. The adhesive may be of a type known in the art, which will secure the visual stimulator to the subject, yet allow it to be removed without damaging the skin. The adhesive portion 210 may be covered by and therefore protected by a release layer (not shown). The release layer may be removed to expose the adhesive when the visual stimulator is to be adhered to a subject.

The frame 202 may include two spaced eye covering portions in the form of lobes 212 connected together at a bridge portion 214 with each lobe defining a recess 216. Each lobe 212 may be a curved or rounded structure that is positioned around one of the subject's eyes. The frame may have an inverted V-shaped notch 216 to accommodate a subject's nose. First side of the frame 204 may curve inwardly from the bridge 214 outwardly toward the ends of the frame. Therefore, the frame 202 is thicker at the ends then at the bridge 214. This curvature assists in closely fitting the visual stimulator 200 to the periocular region of the wearer.

The frame body second side 206 may be relatively flat and may include the light emitting source 218. The light emitting source 218 may include one or more discrete light sources secured to a panel 220. The panel 220 is fixedly secured to the frame second end 206. In a preferred embodiment, the panel 220 may include a circuit board and the light sources may include LED's functionally connected to the circuit board. The light sources may be disposed on the panel such that at least one light is positioned in each lobe recess 216. In this way, each eye will be stimulated with light. The light emitting sources 218 are located at the bottom of the recesses, and are therefore, separated from the subject's eyes by the thickness, T, of the frame. Accordingly, if pressure is exerted on the panel, and some compression of the resilient material occurs, the light sources would not engage the patient's eyes.

Figure 5:
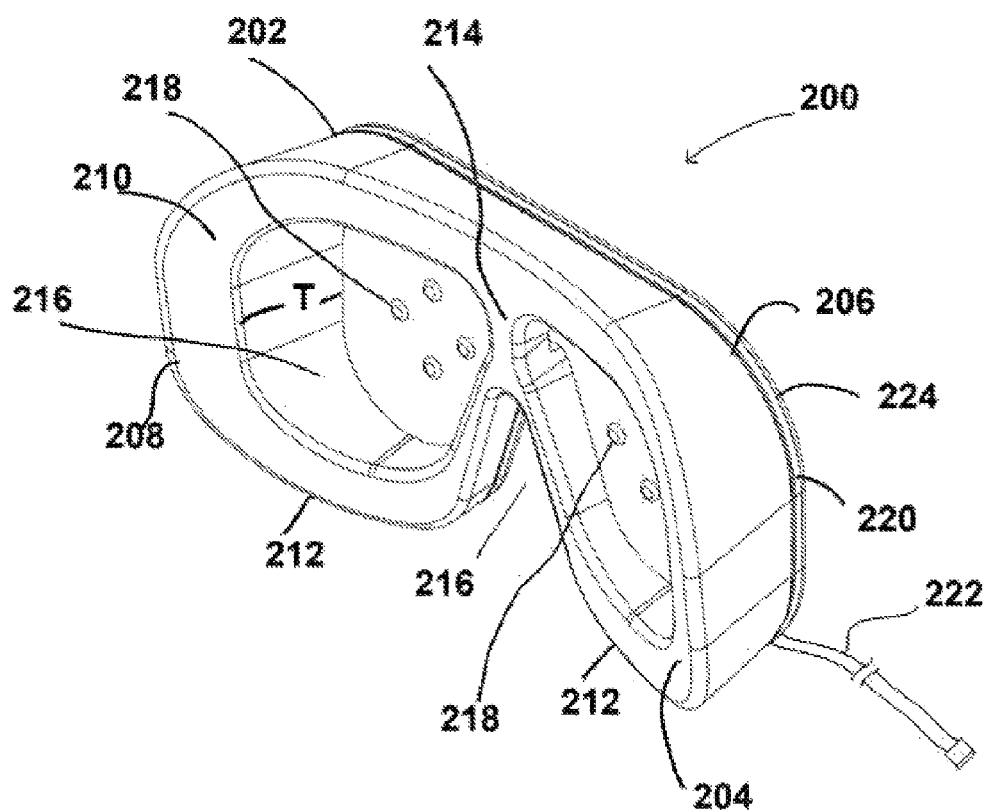
FIG. 5 is perspective view of a further alternative embodiment of a visual stimulator.
Figure 6:
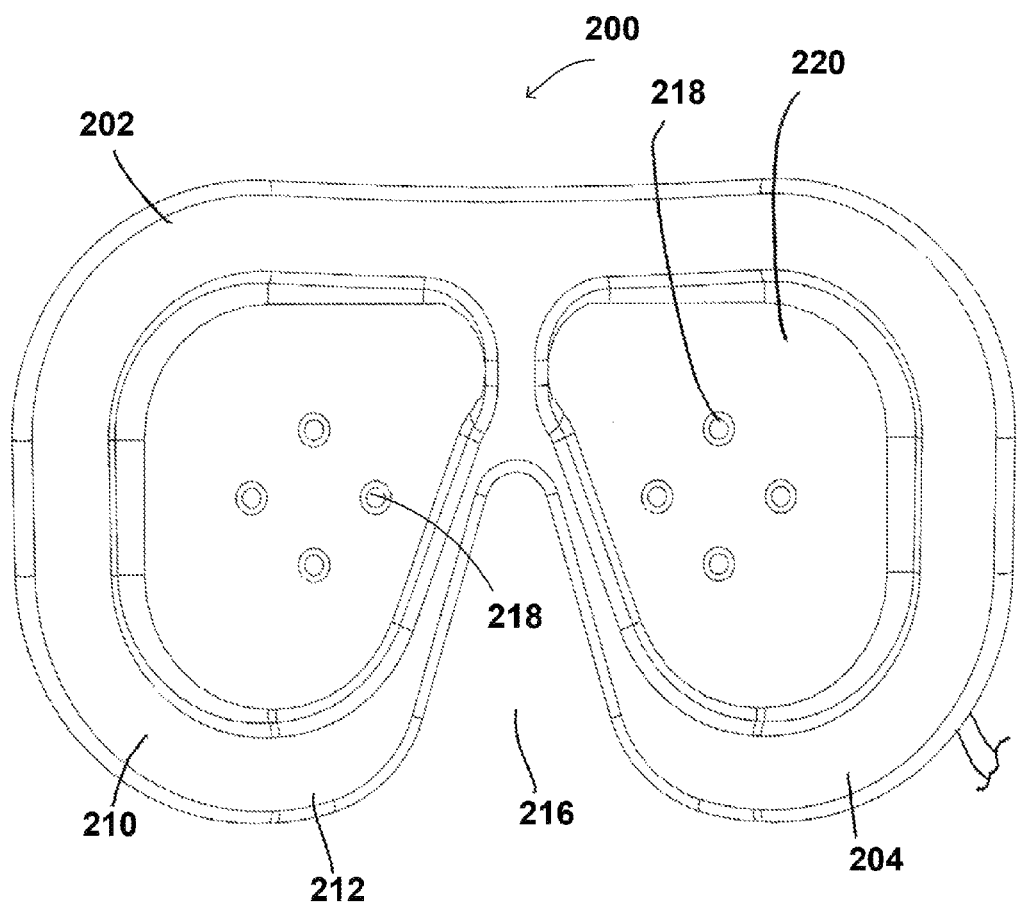
FIG. 6 is a top elevational view of a first side of the visual stimulator of FIG. 5.

The panel 220 may include an interface 222 to operably connect to a triggering device which illuminates the light emitting sources 218 in a controlled manner. The interface may include wires and a connector as shown in FIG. 5. However, it is within the contemplation of the present invention other mode of connection including wireless connectivity may be employed.

When the light emitting sources 218 are triggered and the visual system stimulated, following such stimulation there is the recording of a resultant neurophysiological signal. The resultant neurophysiological signal may be an electroretinogram, optic nerve action potential, or visual evoked potential.

Figure 7:
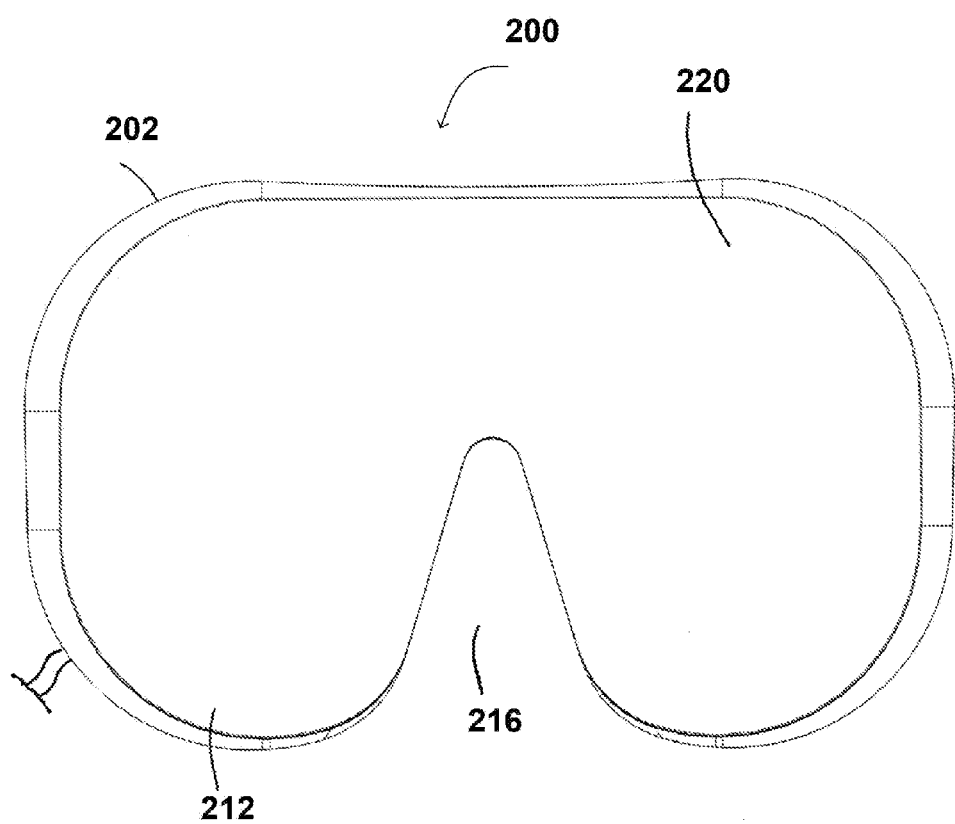
FIG. 7 is a top elevational view second side of the visual stimulator of FIG. 5.
Figure 8:
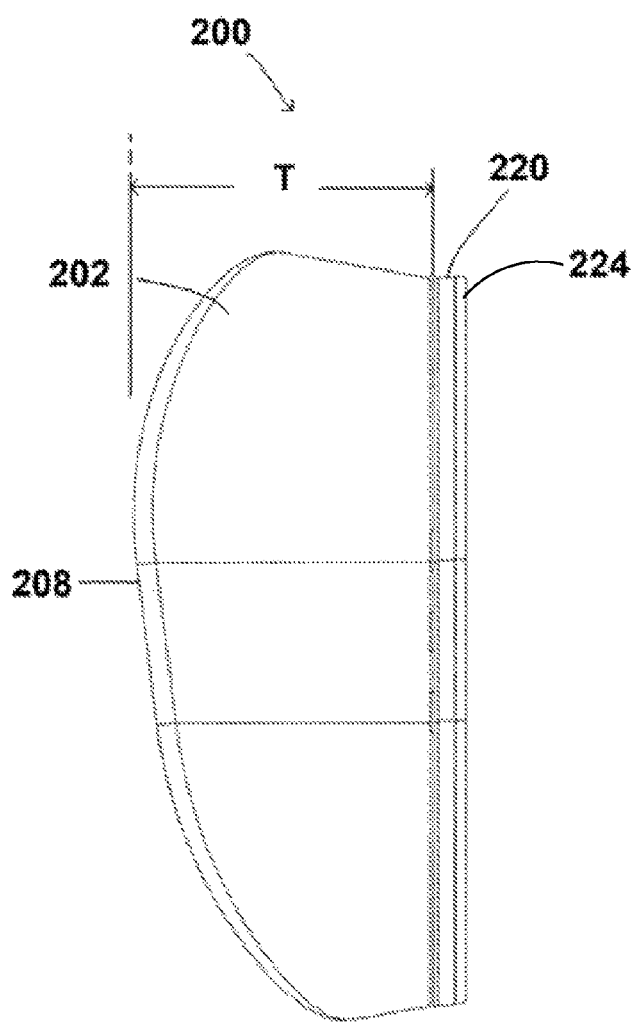
FIG. 8 is a side elevational view of the visual stimulator of FIG. 5

With reference to FIGS. 7 and 8, the panel 220 may further include a backing 224 which is opaque or semi-opaque to restrict the transmission of light out from the visual stimulator. Restricting the light out of the visual stimulator 200 reduces distraction to surrounding healthcare workers. However, it is contemplated that some light may be allowed to escape the visual stimulator to permit an attendant to visually detect that the visual stimulator 200 is operating.

The visual stimulator disclosed herein provided has several advantages including but not limited to:

1.) Hygienic operation. The visual stimulator may be disposable, therefore, it will eliminate the necessity of cleaning and sterilization in between patients. Reusable stimulating goggles must be carefully cleaned and preferably sterilized after each use in the operating room. Additionally, some bodily fluids are extremely difficult to remove without damaging the reusable stimulating goggles. Using a disposable self adhesive visual stimulator will eliminate such problems.

2.) Improved ocular safety. Reusable stimulating goggles may damage the eye, especially during procedures where the patient is placed face down. The visual stimulator consists largely of padding or other soft material and actually will add protection to the eyes rather than increasing the risk of damage caused by prior art devices.

3.) The form fitting and self-adhesive characteristics of the present invention will result in more effective acquisition of data. Prior art devices utilize reusable stimulating goggles which are fastened to the patient's head with rubber or other elastic straps. These straps often interfere with the surgical approach during intracranial procedures, thereby limiting their usefulness. Additionally, stimulating goggles may be accidentally moved from their original position during the operation, as the head is manipulated. It is often impossible to replace the goggles once the surgery has begun. A visual stimulator being secured to the patient by adhesive will eliminate these problems, as there will not be a strap around the entire head and the adhesive properties of the visual stimulator disclosed herein will significantly reduce any chance of the self adhesive visual stimulator moving as the head is manipulated.

4.) The specially designed high intensity light emitting diodes of the visual stimulator disclosed herein in close proximity to the eyes will provide a stronger stimulus than current goggles. Additionally, light sources of different wavelengths/colors may be employed in different arrangements in order to optimize responses.

While the visual stimulator has been described and illustrated with respect to preferred embodiments, it is not intended to limit the invention, except as defined by the following claims. Furthermore, numerous modifications, changes, and improvements will occur to those skilled in the art without departing from the spirit and scope of the invention.

What is claimed is:

1. A device for the stimulation of the visual system comprising:
    a body having a pair of spaced lobes configured to conform to the periocular region, the body having a first side and an opposed second side, the body including a resilient portion disposed on the first side which is engagable with, and conformable to, the periocular region of a wearer; the resilient portion having thereon an adhesive layer engagable with the wearer for securing the body to the periocular region of the wearer; and
    a light emitting source disposed within each of the pair of lobes to selectively illuminate the periocular region.

2. A device as described in claim 1, wherein the body includes a side wall extending between the first and second body sides.

3. A device as described in claim 2, wherein the body sidewall includes an inwardly curved section to accommodate a wearer's nose.

4. A device as described in claim 2, wherein the lobes each define a chamber having a back wall forming an eye covering portion, and the light emitting source is disposed on the eye covering portion in the wear's field of view.

5. A device as described in claim 1, wherein the light emitting source is secured to the second side of the body.

6. A device as described in claim 1, wherein the body includes a resilient portion disposed on the first side which is engagable with, and conformable to, the periocular region of a wearer.

7. A device as described in claim 1, wherein the body is formed of a resilient foam material.

8. A device as described in claim 1 wherein the light emitting source includes at least one light emitting diode disposed in each lobe which interfaces with a triggering mechanism.

9. A device as described in claim 1, wherein the light emitting source includes a plurality of light emitting diodes having different wavelengths.

10. The device as defined in claim 1, wherein the body second side is covered with a panel extending across the body, the panel being at least semi-opaque to attenuate the transmission of light out of the body, the panel having secured thereon the light emitting source for each lobe.

11. A visual stimulator comprising:
    a frame configured to accommodate a wearer's periocular region, the frame having a first eye covering portion and a second eye covering portion, the first and second eye covering portions being separated from each other by a portion of the frame and each of the first and second eye coverings extending over and covering one of a wearer's eyes;

a light emitting source being disposed in the first and second eye covering portions wherein each eye is stimulated by light, the light emitting source being operably connectable to a triggering device for operating the light emitting source in a predetermined sequence; and the frame having a first side and an opposed second side, and the frame first side including a resilient portion engagable with and conformable to a wearer's periocular region, the resilient portion spacing the light emitting source from the frame first side, wherein the light emitting source is spaced from the wearer's periocular region.

12. A visual stimulator as defined in claim 11, wherein the first and second eye covering portions are separated from each other by a bridge and the frame increases in thickness as it extends outwardly from the bridge toward side ends, such that the frame first side is curved to accommodate the periocular region of a wearer.

13. A visual stimulator as defined in claim 11, wherein the frame second side includes a panel secured thereto, and the light emitting source is disposed on the panel.

14. A visual stimulator as defined in claim 13, wherein the frame is formed of a compressible resilient material extending between the first and second frame sides.

15. A visual stimulator as defined in claim 11, wherein the first and second eye covering portions each define a recess and the light emitting source is disposed at the bottom of the recess.

16. A visual stimulator as defined in claim 11, wherein the first frame side includes an adhesive portion engagable with a wearer for securing the frame to the wearer.

17. A visual stimulator as defined in claim 11, wherein the light emitting source includes one or more LED's.

18. A method for assessing visual pathways comprising:
providing a visual stimulator, wherein the visual stimulator comprises a body having resilient padding shaped to conform to a periocular region and an adhesive portion, at least one light emitting source disposed on the body, and a mechanism for interfacing with a triggering device;
adhering the visual stimulator to a periocular region;
stimulating the visual system by triggering the at least one light emitting source with the triggering device; and
detecting and recording neurophysiolocigal signals in response to the stimulating of the visual system.

19. The method of claim 18, wherein the neurophysiological signals include one of an electroretinogram, optic nerve action potential, and visual evoked potential.

20. The method of claim 18, wherein the at least one light emitting diode includes a plurality of light emitting diodes having different colors.

21. The method of claim 18, wherein the at least one light emitting diode includes a plurality of light emitting diodes having different wavelengths.

* * * * *